United States Patent [19]

Price et al.

[11] Patent Number: 5,149,679
[45] Date of Patent: Sep. 22, 1992

[54] GALLIUM-CONTAINING ZEOLITE CATALYSTS

[75] Inventors: Geoffrey L. Price, Baton Rouge, La.; Vladislav I. Kanazirev, Sofia, Bulgaria; Kerry M. Dooley, Baton Rouge, La.

[73] Assignee: Board of Supervisors of Louisiana State University and Agricultural and Mechanical College, Baton Rouge, La.

[21] Appl. No.: 517,334

[22] Filed: May 1, 1990

[51] Int. Cl.$^5$ .......................... B01J 29/06; B01J 23/08
[52] U.S. Cl. ....................................................... 502/61
[58] Field of Search .................... 502/61, 60, 66, 105

[56] References Cited

U.S. PATENT DOCUMENTS

| | | | |
|---|---|---|---|
| 3,702,886 | 11/1972 | Argauer et al. | 423/328 |
| 4,175,057 | 11/1979 | Davies et al. | 502/61 |
| 4,180,689 | 12/1979 | Davies et al. | 585/407 |
| 4,331,774 | 5/1982 | Boersma et al. | 502/61 |
| 4,334,114 | 6/1982 | Ellis | 585/407 |
| 4,350,835 | 9/1982 | Chester et al. | 585/415 |
| 4,377,504 | 3/1983 | Roberts | 502/61 |
| 4,392,989 | 7/1983 | Chu et al. | 252/455 Z |
| 4,490,569 | 12/1984 | Chu et al. | 585/415 |
| 4,548,916 | 10/1985 | Baker | 502/105 |
| 4,565,897 | 1/1986 | Gane et al. | 585/415 |
| 4,605,805 | 8/1986 | Chang et al. | 585/415 |
| 4,613,716 | 9/1986 | McNiff | 585/415 |
| 4,629,818 | 12/1986 | Burress | 585/517 |
| 4,642,403 | 2/1987 | Hyde et al. | 585/415 |
| 4,711,970 | 12/1987 | Chang et al. | 585/415 |
| 4,727,206 | 2/1988 | Clayson et al. | 585/415 |
| 4,746,763 | 5/1988 | Kocal | 585/417 |
| 4,761,511 | 8/1988 | Barlow | 585/415 |
| 4,766,265 | 8/1988 | Desmond et al. | 585/415 |
| 4,822,941 | 4/1989 | Baillargeon et al. | 585/417 |
| 4,855,522 | 8/1989 | Diaz | 585/417 |

OTHER PUBLICATIONS

Gnep et al., "Conversion of Light Alkanes into Aromatic Hydrocarbons. 3. Aromatization of Propane and Propene on Mixtures of HZSM5 and of $Ga_2O_3$," in Karge et al. (Ed.), *Zeolites as Catalysts, Sorbents and Detergent Builders*, pp. 153–162 (1989).

Lang et al., "Tellurium-Loaded Zeolites I. A Novel Dehydrocyclization Catalyst," J. Catalysis, vol. 20, pp. 293–298 (1971).

Price et al., "Tellurium NaX Zeolites II. Nature of Active Sites," J. Catalysis, vol. 81, pp. 369–374 (1983).

Iglesia et al., "Alkane Rearrangement Pathways on Tellurium-Based Catalysts," J. Catalysis, vol. 125, pp. 95–111 (1990).

*Primary Examiner*—Carl F. Dees
*Attorney, Agent, or Firm*—John H. Runnels

[57] ABSTRACT

A catalyst useful in the aromatization of light paraffins and other hydrocarbons conversion reactions, formed by preparing an intimate mechanical mixture of a gallium-containing species, such as $Ga_2O_3$, with a zeolite having a pore mouth comprising 10 oxygen atoms, such as ZSM-5, preferably followed by treatment with a reducing agent, such as hydrogen.

19 Claims, 6 Drawing Sheets

GALLIUM-CONTAINING ZEOLITE CATALYSTS

BACKGROUND OF THE INVENTION

This invention pertains to gallium-containing zeolite catalysts, particularly to gallium-containing zeolite catalysts which are useful in aromatization of light paraffins, and in other hydrocarbon conversion reactions.

Zeolitic materials, both natural and synthetic, are known to have catalytic capabilities for various types of hydrocarbon conversions. Certain zeolitic materials are ordered, porous, crystalline aluminosilicates having a definite crystalline structure within which there are a large number of small cavities which are interconnected by a number of still smaller channels. These cavities and channels are precisely uniform in size. Because the dimensions of these pores will admit molecules of certain dimensions, while rejecting those of larger dimensions, these materials have come to be known as "molecular sieves," and are used in a variety of ways to take advantage of these properties.

U.S. Pat. No. 3,702,886, which is incorporated by reference, describes a family of synthetic zeolites designated as "Zeolite ZSM-5" or simply "ZSM-5," having a characteristic x-ray diffraction patterns and a composition in terms of mole ratios of oxides as follows:

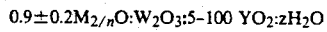

wherein M is a cation, n is the valence of said cation, W is selected from the group consisting of aluminum and gallium, preferably aluminum; Y is selected from the group consisting of silicon and germanium, preferably silicon; and z is between 0 and 40. Crystalline aluminosilicates having the aforesaid composition and characteristic X-ray diffraction pattern are classified as MFI-type zeolites in the Atlas of Zeolite Structure Types by W. M. Meier and D. H. Olson, published by the Structure Commission of the International Zeolite Association (1978), which is incorporated by reference. U.S. Pat. No. 3,702,886 was the forerunner to a number of patents relating to synthetic crystalline aluminosilicate zeolites, all of which are characterized by a high, that is 10:1 or greater, silica to alumina molar ratio, high stability, presence of acid sites, and the ability to catalyze many kinds of conversion reactions, such as cracking, isomerization of n-paraffins and napthenes, polymerization of olefinic and acetylenic compounds, reforming, alkylation, isomerization of polyalkyl substituted aromatics, and disproportionation of aliphatic and alkyl substituted aromatic hydrocarbons. The acid form of a ZSM zeolite may be denoted as an "HZSM."

Gallium-containing zeolites for catalysis, particularly for catalysis of light paraffin aromatization, have received attention recently. Different formulations of such catalysts have included catalysts prepared by ion exchange, by impregnation of ZSM-5 with gallium salts, and by synthesis of galloaluminosilicates.

Gnep et al., "Conversion of Light Alkanes into Aromatic Hydrocarbons. 3. Aromatization of Propane and Propene on Mixtures of HZSM5 and of Ga$_2$O$_3$," in Karge et al. (Ed.), *Zeolites as Catalysts, Sorbents and Detergent Builders*, pp 153-162 (1989) report the use of a mechanical mixture of Ga$_2$O$_3$ and HZSM-5 as a catalyst for the conversion of propane, propene, 1-hexene, 1-heptene, methylcyclohexane and methylcyclohexene. This reference does not discuss the degree of mechanical mixing used, and in particular does not mention any milling of the catalyst; does not mention any reduction or hydrogen pretreatment of the catalyst; and does not mention any time-on-stream increase in catalytic activity. This reference required relatively high weight ratios of gallium to ZSM-5 to achieve modest aromatics selectivity. In FIG. 1 of Gnep et al., the lowest elemental weight percentage of gallium in the catalyst (corresponding to 5 mg Ga$_2$O$_3$/25 mg HZSM5) may be calculated to be approximately 12.4%, which was reported to give an aromatics yield of less than ¼% at a total propane conversion of about 5%, or an aromatics selectivity of less than 5% (the ratio of aromatics yield to total conversion). In the same FIG. 1 of Gnep et al., where the elemental weight percentage of gallium was approximately 55.8% (corresponding to 75 mg Ga$_2$O$_3$/25 mg HZSM5), the aromatics yield was reported to be about 1½% at a total propane conversion of about 8¾%, or an aromatics selectivity of about 17%. In FIG. 3 of Gnep et al., for the same approximately 55.8 wt % gallium catalyst, at a total reported propane conversion of about 23.5%, the reported aromatics yield was about 10%, or an aromatics selectivity of about 42.5%. In the same FIG. 3 of Gnep et al., for the approximately 12.4 wt % gallium catalyst, at a total reported propane conversion of about 11.3%, the reported aromatics yield was about 1.6%, or an aromatics selectivity of about 14%.

U.S. Pat. No. 4,642,403 describes the preparation of gallium/zeolite catalysts by impregnation or ion-exchange. It discusses activation of the catalyst by heating from 400° C. to 650° C., preferably from 500° C. to 600° C. It states that activation may be carried out in an atmosphere consisting of hydrogen, air, steam, or a gas inert under the reaction conditions such as nitrogen, but preferably in an atmosphere containing oxygen. It describes in-situ hydrogen treatment for 2 hours at 550° C. prior to testing for hydrocarbon conversion activity.

U.S. Pat. No. 4,766,265, Catalysts for the Conversion of Ethane to Liquid Aromatic Hydrocarbons, mentions treating HZSM-5 with a source of gallium, aluminum, and/or zinc, by ion exchange, impregnation, gas phase displacement, or other known methods of incorporating the metal into the molecular sieve. The preferable metal is stated to be gallium, and the reference describes incorporating gallium by impregnation or ion-exchange with a gallium-containing solution. This reference teaches the desirability of additionally further treating the gallium-loaded zeolite both with rhenium, and with a metal selected from the group consisting of nickel, palladium, platinum, rhodium, and iridium. This reference describes conversions of ethane, so its reported experimental results are not directly comparable to those described below for conversion of propane. With that caveat, a total paraffin conversion in Table I of 48.3% was reported, obtained with a Ga/Re/Rh/HZSM-5 catalyst at 640° C., WHSV=0.73, with an aromatics selectivity of 60.0%; but with a high 27.1% selectivity for methane, an undesired product. Table I of this reference reports catalysts with higher aromatics selectivities, but at lower total paraffin conversions. Table I of this reference also reports catalysts with lower methane selectivities, but at lower total conversions, lower aromatics selectivities or both. This reference discusses no pretreatment to activate the catalysts, other than heating in nitrogen to the reaction temperature.

U.S. Pat. No. 4,761,511 teaches the wet preparation of certain crystalline galloaluminosilicates, and states

3 that steam-modified galloaluminosilicates showed increased catalysis of hydrocarbon aromatization. Aromatics selectivities up to 57.7% were reported for butane conversion, and up to 55% for propane conversion.

SUMMARY OF THE INVENTION

The preparation of intimate mechanical mixtures of a gallium-containing species, such as $Ga_2O_3$, with a zeolite having a pore mouth comprising 10 oxygen atoms, such as ZSM-5, has created efficient catalysts for the aromatization of light paraffins at lower levels of gallium than reported in the prior art. At propane conversions between 49.8% and 64.0%, the selectivity for aromatics was above 60%, with gallium loadings as low as 2 wt %, following pretreatment of the catalyst with a reducing agent such as hydrogen. Corresponding selectivities for less desirable methane have been observed to be as low as 12% or less.

Catalysts with gallium loadings of 5 wt % (on an elemental basis) have given propane conversions as high as 87.5%, with aromatic selectivities of 77.0% and methane selectivities of 6.9%, following pretreatment of the catalyst with hydrogen.

Without hydrogen pretreatment, catalysts of the present invention have shown aromatic selectivities in propane conversion of over 50%, with gallium loadings of only 2 wt % (on an elemental basis).

The selectivity of these catalysts for aromatization of propane is superior to that reported for prior art gallium/ZSM-5 catalysts, even with lower gallium loadings than reported in the prior art catalysts. A high degree of mechanical mixing has been found to be important for achieving these superior results. The catalysts have a low selectivity for conversion to methane, especially when compared to their aromatic selectivity.

Without a reducing pretreatment, the activity of these catalysts increases, to a point, with time on stream with hydrocarbon feeds at elevated temperatures; the activation may be accelerated, and aromatics selectivity improved, by pretreatment with a reducing agent such as hydrogen gas. Unlike some prior art catalysts, these catalysts do not necessarily require additional treatment with rhenium, nickel, palladium, platinum, rhodium, or iridium. The catalysts do not require steaming.

The catalysts may also be used for other hydrocarbon conversion reactions.

Preparation of a quality catalyst of the present invention has the additional advantage of requiring no wet or liquid-phase procedures.

DETAILED DESCRIPTION OF THE INVENTION

Figure 1:
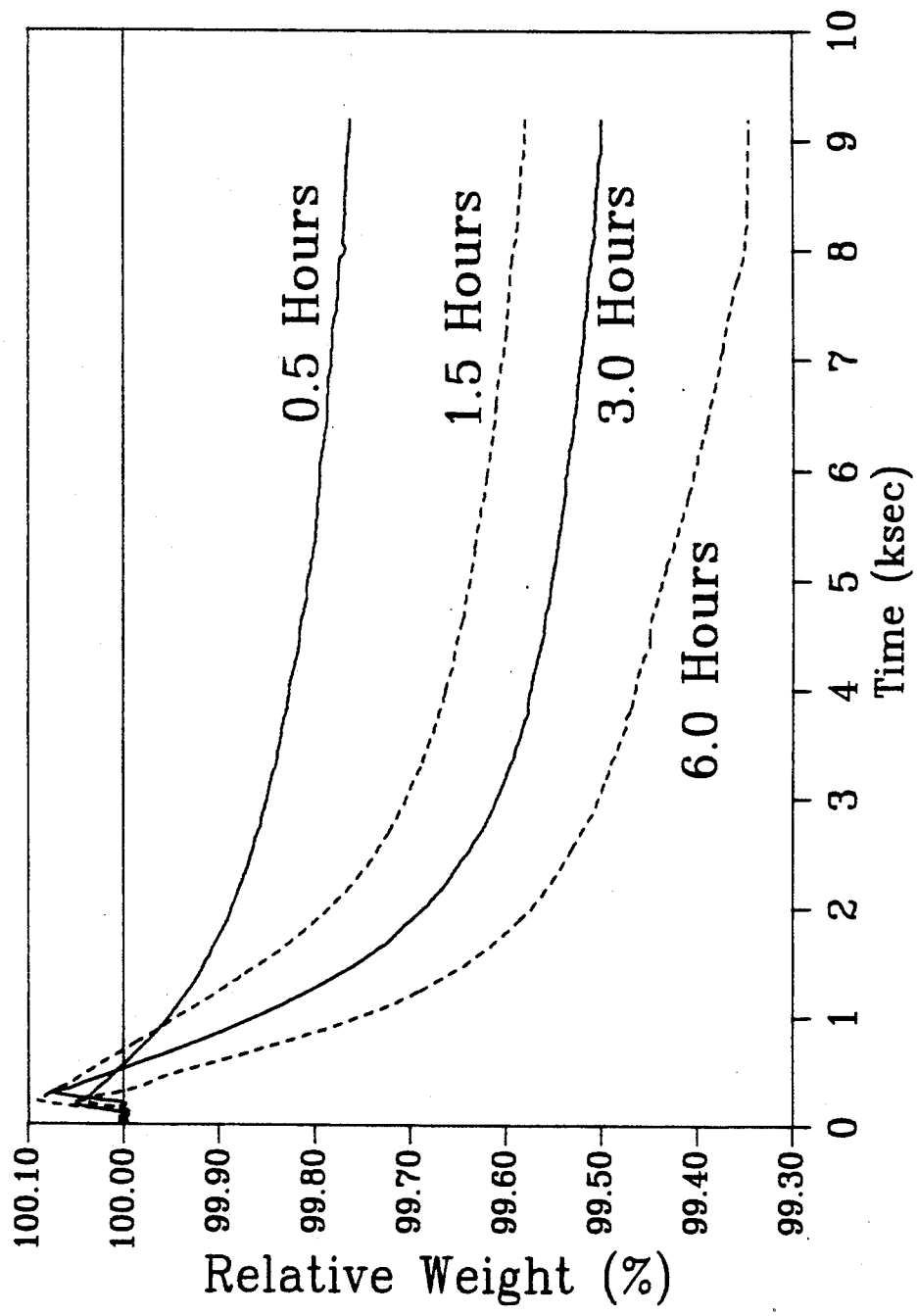
FIG. 1 illustrates the relative weight loss during hydrogen reduction of KPD-2 catalysts prepared with different ball-milling times.

Catalysts of the present invention were prepared by making an intimate mechanical mixture of a suitable zeolite with a suitable gallium-containing compound. This preparation was preferably followed by reduction, such as in hydrogen gas.

The zeolites used as a base, or starting material, suitably have a silica to alumina molar ratio between 20:1 and 150:1, preferably between 30:1 and 50:1, and may be selected from zeolites of the general formula:

$$1.0 \pm 0.4 M_{2/n}O : Al_2O_3 : ySiO_2 : zH_2O$$

wherein M is a cation of valence n, y is between 5 and 100, and z is between 0 and 40. The cation M is preferably $H^+$ or $NH_4^+$.

The zeolite should preferably have a pore mouth comprising 10 oxygen atoms, and is preferably a ZSM-5, ZSM-11, or ZSM-12 zeolite. For descriptions of these zeolites and methods of making them, see U.S. Pat. No. 3,702,886, U.S. Pat. No. 3,709,979, and U.S. Pat. No. 3,970,544, each of which is incorporated by reference.

The source of gallium used by the inventors was $\beta$-$Ga_2O_3$. Other possible sources of gallium include gallium nitrate, other gallium salts, alkali metal gallates, other phases of gallium oxide, and gallium suboxide. The amount of gallium present in the catalyst, on an elemental basis by weight, may vary between 0.05% and 200%, and is preferably between 0.5% and 10%.

This general type of catalyst may be called a "KPD" catalyst, with a numerical suffix indicating the amount of gallium loading, on elemental basis by weight percentage. For example, a 2 wt. % gallium catalyst is called "KPD-2."

A binder may be added to aid in fabricating the catalysts into a suitable form. Binder materials which may be used include clays, alumina, silica, silica-alumina, and graphite. The finished catalyst may contain binder amounts of between zero and about 95% by weight, more preferably between about 10% and about 50% by weight. The preferred binder material is silica, which can be incorporated in colloidal form from materials such as Ludox ® AS-30 or AS-40, available from DuPont. Silica is known not to interfere with the activity of other zeolite catalysts, and additionally is known not promote side reactions, such as coking.

An "intimate mechanical mixture" or "intimate physical mixture" of different components is one whose degree of mixing is such as to result in a significant increase in catalytic activity over the catalytic activity of a simple, brief mixture of those same components. Suitable apparatus for making intimate mechanical mixtures include ball mills, hammer mills, roller mills, ribbon mills, gear mills, jaw crushers, gyrotory crushers, cone crushers, pan crushers, single or two roll crushers, mortar and pestle, vibrating mills, rotary crushers, or bowl mills. An intimate mechanical mixture of the components of the catalyst of the present invention gave unexpected results, namely a high aromatics selectivity and a low methane selectivity in the conversion of propane, at high total propane conversions.

The present invention concerns novel catalysts and methods for making such catalysts. The present invention also provides a process for the production of aromatic hydrocarbons, which comprises contacting the novel catalyst with vapor-phase $C_2$ to $C_{12}$ hydrocarbon feed, preferably a $C_2$ to $C_6$ hydrocarbon feed, most preferably a $C_2$ to $C_4$ hydrocarbon feed.

By $C_2$ to $C_{12}$ hydrocarbon feed is meant a feed containing either a single hydrocarbon component, or a mixture of saturated or unsaturated $C_2$ to $C_{12}$ hydrocarbons. The feed is preferably one or more saturated or unsaturated $C_2$ to $C_6$ hydrocarbons, and is most preferably one or more saturated or unsaturated $C_2$ to $C_4$ hydrocarbons. Hydrocarbon feeds may contain one or more of the following compounds: ethane, ethylene, propane, propylene, butane, 1-butene, 2-butene, isobutane, and isobutene. The reaction temperature should be maintained between temperatures of from about 400° C. to about 750° C., preferably from 500° to 575° C. Pressure is not critical, and can be from ambient to about 20 atmospheres, and is preferably from ambient to about 10 atmospheres. The feed rate may range from about 0.05 to about 50 parts by weight reactant to weight of total catalyst per hour (WHSV), and is preferably from about 0.1 to about 10 WHSV.

Adding small amounts (less than 10%) of oxygen gas to the hydrocarbon feed may improve the activity of hydrocarbon conversions, particularly conversion of ethane.

Adding noble metals to the zeolite, such as one or more of the group consisting of rhenium, rhodium, nickel, palladium, platinum, and iridium may improve the activity or selectivity of the catalysts of the present invention.

Two bases were used to prepare the catalyst. The first, used in all examples below except where noted otherwise, was Union Carbide Co., Linde Div. ELZ-105-6, an HZSM-5 material. The ELZ-105-6 zeolite used in these experiments had the following characteristics as reported by the manufacturer: the zeolite was hydrophobic, organophilic, thermally stable to at least 1000° C., and stable in the presence of steam or strong mineral acids. It was the hydrogen form of the zeolite, and was highly siliceous, having a $SiO_2/Al_2O_3$ molar ratio over 40. Typical chemical compositions, on an anhydrous basis by weight, were reported to be: $SiO_2$ (94.95–95.9%), $Al_2O_3$ (3.7–3.73%), $Na_2O$ (0.03–0.04%), $K_2O$ (0.01%), $Fe_2O_3$ (0.26%), $MgO$ (0.05%), $TiO_2$ (0.05%), $ZrO_2$ (0.03%). Surface area was reported to be 401 m²/g (by the 1 pt. BET method). The percent $O_2$ absorbed, at 100 Torr and −183° C., was reported to be 16.5%. The size of the free aperture was reported as 6.0 A°. The pore volume was reported to be 0.16 cm³/g. The crystal density was stated as 1.8 g/cm³. The largest molecules adsorbed were stated to be $SF_6$ and benzene. The ELZ-105-6 was supplied in powder form.

The second base used in preparing the catalysts, to date used only for the experiments whose results are reported below in Table 7, was a zeolite sold commerically by UOP under the name MFI, lot number 13923-573. This zeolite was reported by the manufacturer to be a ZSM-5 zeolite having a $SiO_2/Al_2O_3$ molar ratio of 40, which had been acid washed and calcined.

All or most zeolites, particularly acidic zeolites, having a pore mouth comprising 10 oxygen atoms should also work in preparing catalysts of the present invention.

Figure 2:
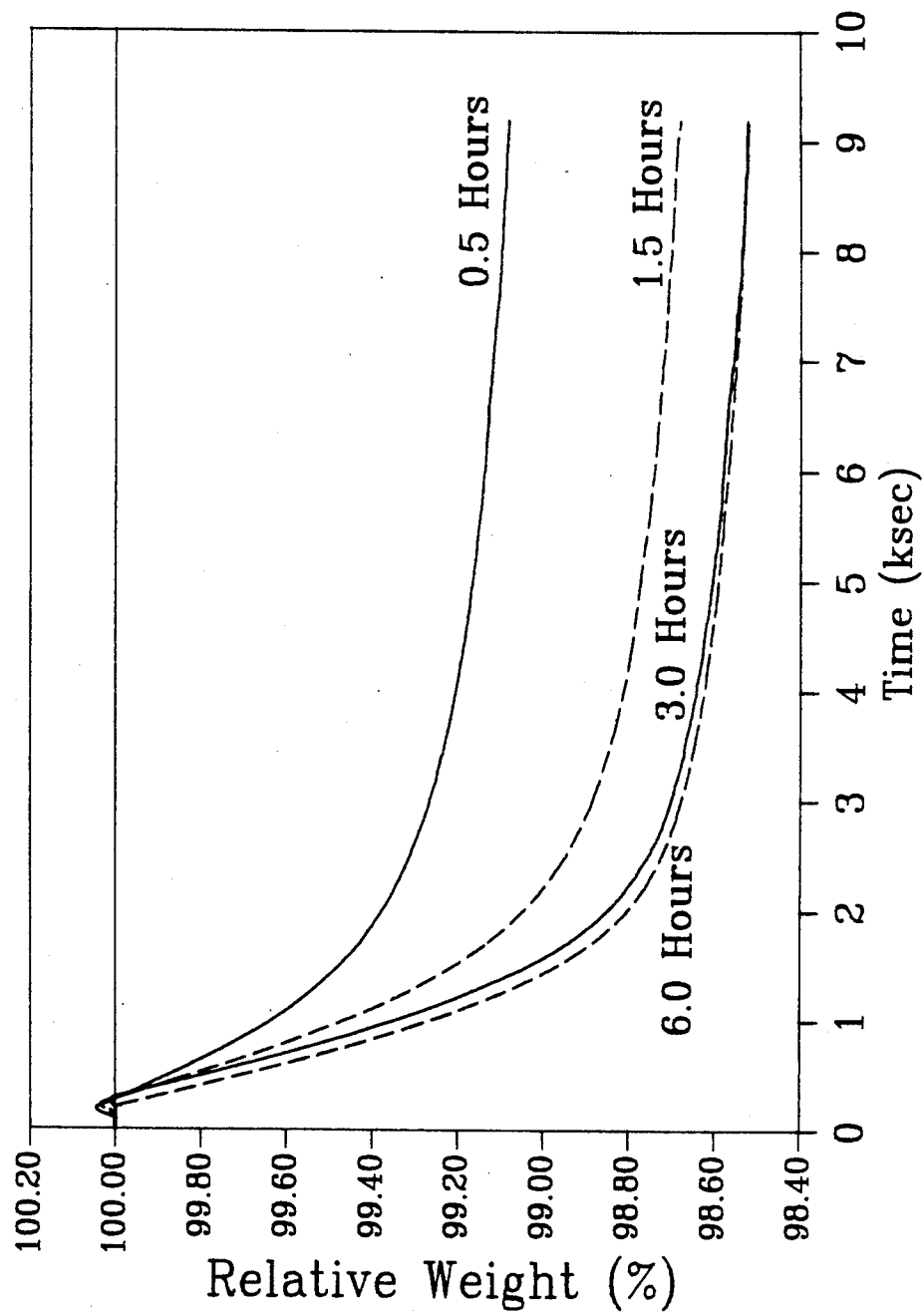
FIG. 2 illustrates the relative weight loss during hydrogen reduction of KPD-10 catalysts prepared with different ball-milling times.

A gallium-containing catalyst was prepared by ball-milling β-$Ga_2O_3$(4N5-grade, lot #3038, Ingal International Co.) with the HZSM-5 base for 3 hours. The chamber of the ball mill was 3 inches deep, had a 5 inch inner diameter, and was rotated at 86 rpm. Twenty grams of material was placed in the ball-mill. Sixty-five stainless steel balls were used: 30, ¼-inch diameter; 20, ⅜-inch diameter; and 15 ½-inch diameter. The degree of mixing is influenced by many factors—e.g., the number and weight of the balls used in a ball mill, the time of grinding etc. At this time, the inventors know of no better way to quantify the time of grinding and mixing required than empirical observations of what works for a given means of mixing. See FIGS. 1 and 2, showing the relative weight loss during $H_2$ reduction for KPD-2 and KPD-10, respectively, as a function of time of ball-milling for the ball-milling system used by the inventors. (Further details regarding the techniques of the weight loss experiments are given in the section on "Characterization of the Catalysts.")

The catalyst, in the form of particles with 40–60 mesh size, was loaded in a stainless steel tubular reactor (10 mm ID), and heated by a digitally controlled electric furnace. Prior to use, the catalyst was pretreated either in He (60 cm³/min) or in a $H_2$/He mixture (130 cm³/min He and 30 cm³/min $H_2$) by temperature programming as follows: room temperature up to 393K (2K/min), hold at 393K for 2h, 393K to 848K (1K/min), hold at 848K for 2h.

Matheson instrument grade propane, containing about 250 ppm $C_2H_4$, and roughly 100 ppm $C_3H_6$, and high purity He or He/$H_2$ were fed through digital flow controllers, and mixed in the proper ratio before the reactor inlet. The pressure in the system was kept constant by means of a backpressure regulator. Product condensation was inhibited by heating most lines downstream from the reactor outlet, and by using additional He diluent in the effluent in the untraced lines.

The total gas flow rate in the reactor was at least 130 cm³/min at WHSV from 0.4 to 1.2. Experiments were conducted at a nominal total pressure of 123 kPa.

Reactor products were analyzed on-line with a Hewlett-Packard 5880 gas chromatograph equipped with an FID dector; 30 m, wide bore capillary column (Supelco SPB-1); automated gas sampling valve injection; and cryogenic oven.

EXAMPLES

Table 1 details observed reaction products from propane using KPD-10, $H_2$ pretreatment at 803K, and a reaction temperature of 803K, and WHSV=1. The $C_5+$ non-aromatics were primarily n- and i-pentane. The $C_9$ aromatics were primarily trimethylbenzenes. The $C_{11}+$ aromatics were primarily methylnapthalenes.

TABLE 1

| Component | Weight % |
|---|---|
| Methane | 1.851 |
| Ethylene | 3.368 |
| Ethane | 1.874 |
| Propylene | 4.164 |
| Propane | 78.780 |
| i-Butane | 0.151 |
| 1-Butene + i-Butene | 0.313 |
| 1, 3 Butadiene | 0.022 |
| n-Butane | 0.237 |
| t-2-Butene | 0.031 |
| c-2-Butene | 0.098 |
| $C_5+$ non-aromatics | 0.064 |
| Benzene | 3.689 |
| Toluene | 3.512 |
| Ethylbenzene | 0.087 |
| m- & p-Xylene | 1.098 |
| Styrene | 0.023 |
| o-Xylene | 0.324 |
| $C_9$ Aromatics | 0.167 |

TABLE 1-continued

| Component | Weight % |
|---|---|
| Naphthalene | 0.022 |
| $C_{11}{}^+$ Aromatics | 0.024 |

Table 2 compares the reaction of propane over the HZSM-5 substrate with the reaction over KPD-2 at 2 hours on stream, and at 30 hours on stream; in all three cases, without any $H_2$ treatment. The temperature was 803K, with WHSV = 1. In Table 2 and in subsequent tables, the "percent conversion" column refers to the percentage of total feedstock reactant which was converted during the reaction; while the selectivity for a product refers to the weight of that product, divided by the total weight of all products. Table 2 illustrates that when first put on stream, KPD-2 did not exhibit activity and selectivity much different from that of HZSM-5. However, a significant increase in aromatics production, with a concurrent decrease in methane, was evident after 30 hours on stream. This trend continued in an experiment which lasted longer than one week.

TABLE 2

| Catalyst | Time | Percent Propane Conversion | Selectivity, wt % | | | |
|---|---|---|---|---|---|---|
| | | | Aromatics | $C_2$'s | $C_4$'s | $CH_4$ |
| HZSM-5 | | 10.2 | 1 | 64 | 4 | 31 |
| KPD-2 | 2 hr. | 9.1 | 3 | 62 | 4 | 31 |
| KPD-2 | 30 hr. | 11.9 | 12 | 63 | 8 | 17 |

Hydrogen treatment accelerated this activation process, as shown in Table 3 for a reaction run at 803K and WHSV = 1. The upper line shows the product distribution obtained from a KPD-2 catalyst which was first put on stream with propane for 30 hours, followed by 2 hours of $H_2$ at 848K, and subsequently returned to propane. The product distribution was virtually identical to the distribution shown in the lower line, which depicts a KPD-2 catalyst which was treated with $H_2$ at 848 K. for two hours prior to any propane feed.

Without hydrogen pretreatment, activation periods can be lengthy—depending on reaction parameters, the inventors have observed activation periods of up to a week.

TABLE 3

| Treatment | Percent Propane Conversion | Selectivity, wt % | | | |
|---|---|---|---|---|---|
| | | Aromatics | $C_2$'s | $C_4$'s | $CH_4$ |
| 30 hr. $C_3H_8$/2 hr. $H_2$ | 25.1 | 52 | 29 | 5 | 14 |
| 2 hr. $H_2$ | 21.3 | 51 | 31 | 6 | 13 |

Table 4 gives a comparison of the product distributions at 803 K. and WHSV = 1, observed using KPD-2, KPD-5, and KPD-10 with $H_2$ pretreatment at 848 K. for 2 hours. Higher Ga loadings were observed to reduce the total activity, but also strongly to reduce the selectivity to methane, concurrently with a slight decrease in aromatics selectivity, and an increase in $C_4$'s selectivity.

TABLE 4

| Catalyst | Percent Propane Conversion | Selectivity, wt % | | | |
|---|---|---|---|---|---|
| | | Aromatics | $C_2$'s | $C_4$'s | $CH_4$ |
| KPD-2 | 21.3 | 52 | 29 | 5 | 14 |
| KPD-5 | 9.5 | 49 | 35 | 7 | 9 |
| KPD-10 | 5.5 | 46 | 36 | 12 | 6 |

Table 5 gives a comparison of KPD-2, 5, and 10, at 803 K. and WHSV = 1, at 30, 7.5, and 4.5 hours on stream with propane, respectively, and with no hydrogen treatment. Table 5 illustrates that the higher the initial $Ga_2O_3$ loading, the faster the propane activation process proceeded.

TABLE 5

| Catalyst | Time (hrs.) | Percent Propane Conversion | Selectivity, wt % | | | |
|---|---|---|---|---|---|---|
| | | | Aromatics | $C_2$'2 | $C_4$'s | $CH_4$ |
| KPD-2 | 30.0 | 11.9 | 11 | 54 | 6 | 29 |
| KPD-5 | 7.5 | 14.9 | 37 | 37 | 7 | 19 |
| KPD-10 | 4.5 | 18.5 | 45 | 33 | 6 | 16 |

The examples in Tables 6 and 7 illustrate results for the aromatization of propane using catalysts of the present invention. The experimental procedures outlined above were followed, except as noted below. The general conditions applicable to all the following examples were the following: The prepared catalysts were pelletized, crushed, and sieved to 40-60 mesh, and tests were run using 0.8 gram of catalyst. In Table 6, a flow of 0.022 mol/h (1.2 WHSV) of propane in helium, with a propane partial pressure of 14 kPa, and a total pressure of 123 kPa was used. In Table 7, a flow of 0.0055 mol/h (0.4 WHSV) of propane in helium, with a propane partial pressure of 3.5 kPa and a total pressure of 123 kPa was used. In Table 7 only, the zeolite base used to prepare the catalyst was UOP's MFI rather than the Linde ELZ-105-6. The catalysts were each pretreated with $H_2$ for 2 hours at 848 K. This hydrogen pretreatment gave higher aromatics selectivities than were observed, for example, in Tables 3 and 4. Hydrogen pretreatment is thus a preferred mode of making and using catalysts of the present invention.

TABLE 6

| Catalyst | Temp. (K) | Percent Propane Conversion | Selectivity, wt % | | | | |
|---|---|---|---|---|---|---|---|
| | | | Aromatics | $C_2$'s | $C_4$'s | $C_5$'s | $CH_4$ |
| KPD-2 | 803 | 49.8 | 65.6 | 20.5 | 2.4 | 0.2 | 11.4 |
| KPD-2 | 823 | 50.9 | 64.5 | 21.9 | 2.2 | 0.3 | 11.3 |
| KPD-2 | 848 | 64.0 | 64.5 | 21.9 | 1.4 | 0.2 | 12.0 |
| KPD-5 | 848 | 30.1 | 59.5 | 29.8 | 4.4 | 0.4 | 5.7 |
| KPD-10 | 803 | 47.8 | 66.2 | 20.5 | 2.6 | 0.4 | 10.5 |
| KPD-10 | 773 | 26.1 | 64.5 | 21.1 | 5.1 | 0.3 | 9.1 |

TABLE 7

| Catalyst | Temp. (K) | Percent Propane Conversion | Selectivity, wt % | | | | |
|---|---|---|---|---|---|---|---|
| | | | Aromatics | $C_2$'s | $C_4$'s | $C_5$'s | $CH_4$ |
| KPD-5 | 773 | 75.3 | 75.3 | 16.3 | 0.8 | 0.0 | 7.6 |
| KPD-5 | 803 | 74.2 | 74.6 | 17.2 | 0.5 | 0.0 | 7.7 |
| KPD-5 | 823 | 87.5 | 77.0 | 15.8 | 0.2 | 0.1 | 6.9 |

The superior results obtained with the catalysts of the present invention are clearly shown in Tables 6 and 7, particularly Table 7. At a total conversion of 87.5%, an aromatic selectivity of 77% has been achieved with a methane selectivity under 7%.

"Conversion conditions" for a hydrocarbon conversion are conditions of temperature, pressure, flow rate, and other parameters suitable for promoting that hydrocarbon conversion. Suitable conversion conditions for propane conversion, e.g., were described in the above examples.

Characterization of the Catalysts

Based on various investigations into the KPD catalysts, the inventors have developed hypotheses as to the likely character of those catalysts. These investigations and hypotheses are set forth in the remainder of this section, because the inventors hope that they will prove useful. However, the inventors do not intend thereby to be bound by any particular hypothesis or theory.

Microbalance experiments were performed in a Perkin-Elmer TGA-7 microbalance interfaced to an IBM PS/2 computer with a Perkin-Elmer TAC-7 interface. Balance purge gas was 80 cm$^3$/min of He, and reagent gas was 40 cm$^3$/min of an $H_2$/He mixture which could be varied in composition from 0 to 75% $H_2$. Both temperature programmed experiments and isothermal experiments were performed.

X-ray diffraction was obtained with a Scintag PAD-V X-ray diffractometer, equipped with a CuK-alpha radiation source, operated at 1.6 KW, and a Kevex Peltier-cooled solid state silicon detector. The system was completely automated with a Micro VAX II computer using software which allowed background subtraction, CuK-alpha-2 stripping, peak location, deconvolution, and lattice constant calculations. All reported spectra have been background corrected and CuK-alpha-2 stripped.

Exact angle correction was performed using a NaA zeolite external standard prepared by Charnell's recipe, and by assigning actual reflection angles by comparison with the computed powder pattern of von Ballmoos. See Charnell, J. F., *J. Crystal Growth* 8, 291 (1971); and Von Ballmoos, R., "Collection of Simulated XRD Powder Patterns for Zeolites," Butterworths (1984), each of which is incorporated by reference.

X-ray diffraction samples were prepared by placing approximately 20 mg of sample on a glass slide (approximately 2 cm × 2 cm), adding a drop of water, and smearing the sample uniformly over the slide. The samples were dried at 383 K. for two hours, and placed in a desiccator over 1 molar $NH_4Cl$ solution for at least 10 hours prior to a diffraction experiment. Samples prepared in this manner were compared with samples mounted via the more conventional technique of pressing the material in a 1 mm deep planchet. Spectra of samples on glass slides showed about a 30% decline in reflection intensity, and a minor amorphous background from the slide itself—which was removed by background subtraction.

Spectra were recorded from 3° to 60° 2-theta (2 times theta, where theta is the Bragg angle) at 1°/min. Unit cell sizes were calculated by assigning Miller indices to the ZSM-5 bands by comparison with the computed pattern of von Ballmoos, op cit. To measure $\beta$-$Ga_2O_3$ content, the sum of the peak heights at about 31.61° and 35.12° 2-theta ($\beta$-$Ga_2O_3$ lines), divided by the sum of the peak heights at about 24.25° and 29.16° 2-theta (ZSM-5 lines) was assumed to be proportional to the $Ga_2O_3$/ZSM-5 ratio. These lines were selected because of their relative proximity, and because they were well resolved from other bands. A calibration curve for these two parameters, which showed good linearity, was constructed from the catalysts which had been prepared by ball-milling $\beta$-$Ga_2O_3$ with the HZSM-5, but had not been subjected to chemical conditioning. $Ga_2O_3$ contents of unknown samples were determined by using this calibration.

Figure 3:
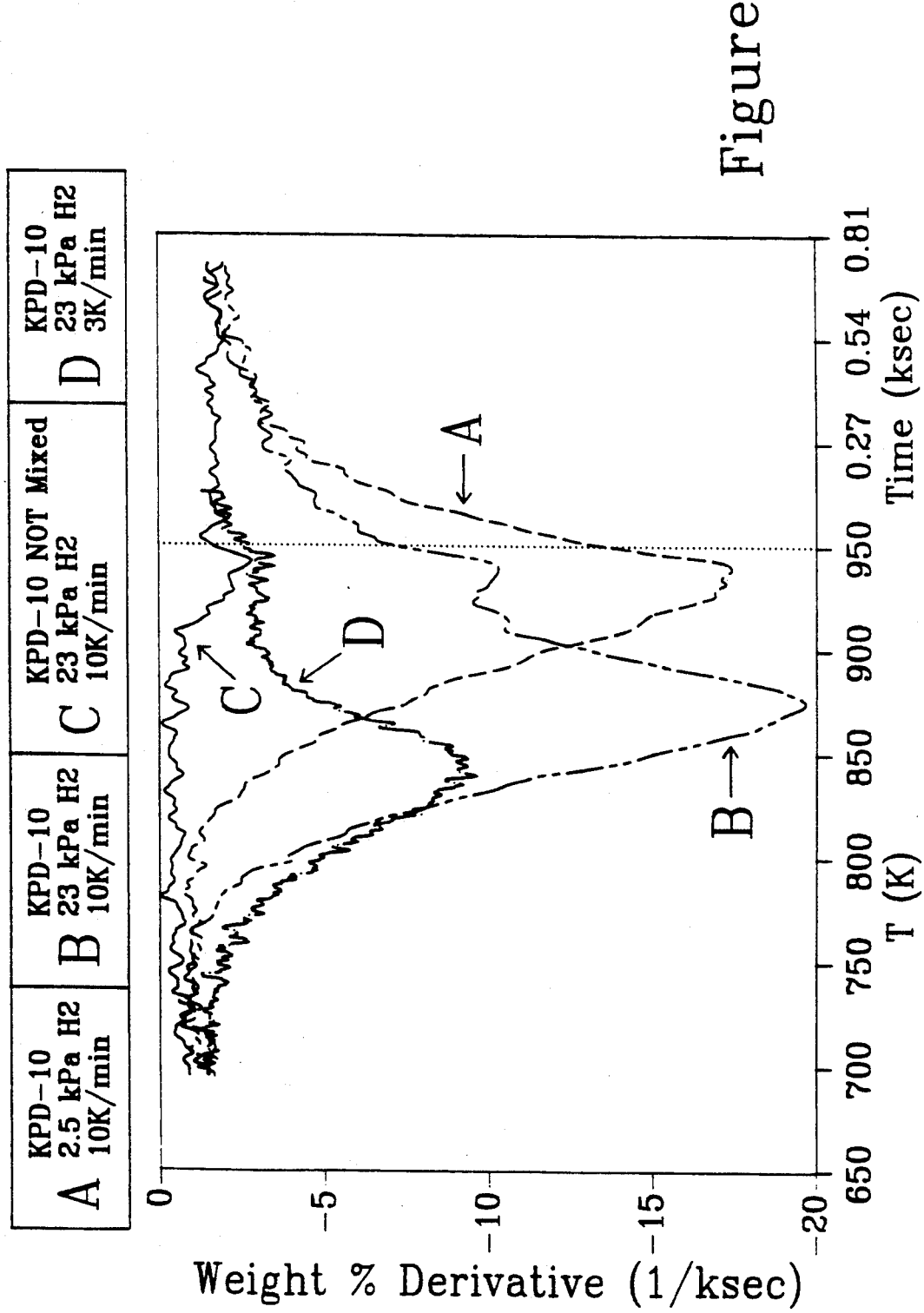
FIG. 3 illustrates the weight % derivative in several temperature-programmed hydrogen reductions of KPD-10 catalyst.

Because reduction appeared to be a critical process in the formation of an active catalyst, characterization of the process was performed in a microbalance. FIG. 3 depicts several typical temperature programmed reductions (TPR), which demonstrate the effect of $H_2$ partial pressure, programming rate, and the intimacy of the physical mixture.

Note in FIG. 3 the weight loss band at about 940 K. for the sample treated at 10 K./min with $P_{H2}=2.5$ kPa (curve A). This band is believed to result from hydrogen reduction of $Ga_2O_3$, as shown by the following evidence, which supports the conclusion that the band is not due to other effects such as dehydration, dehydroxylation, or other elimination processes from the $Ga_2O_3$ or the HZSM-5. First, the band shifted to 875 K. when the hydrogen partial pressure was increased to $P_{H2}=23$ kPA with the programming rate held constant at 10 K./min (curve B). Second, when the programming rate was reduced to 3 K./min (holding the $H_2$ pressure at 23 kPa), the band shifted to about 845 K. (curve D). This indicated a kinetic or diffusion controlled process which involved hydrogen. Third, neither HZSM-5 nor $Ga_2O_3$ individually showed this band. In fact, $\beta$-$Ga_2O_3$ exhibited less than 0.2% weight reduction upon temperature programming to 1000 K. in hydrogen. This suggested that an intimate physical mixture of HZSM-5 and $Ga_2O_3$ was necessary for the reduction to proceed. To test this hypothesis, $Ga_2O_3$ and HZSM-5 were added without mixing in the microbalance pan. No reduction band was noted up to 950 K. with $P_{H2}=23$ kPa (FIG. 3, curve C). Finally, a mixture of $Ga_2O_3$ and NaX zeolite did not appear to undergo reduction in hydrogen under identical conditions, including identical mixing conditions. Therefore, it appeared that both the intimate physical mixture and the zeolite acidity were necessary before the reduction process would occur.

Isothermal microbalance experiments were useful in quantitative determinations of weight loss. In these experiments, the specimen was dried isothermally at 880 K. in He until a constant weight was observed, and the sample was then brought to its reduction temperature (815 K., 842 K., or 870 K.). $H_2$ at $P_{H2}=23$ kPa was then substituted for a portion of the He, so that the overall purge rates in the microbalance remained constant. The reduction process was observed to be a monotonic decline in the specimen weight, until a new stable weight was established.

Figure 4:
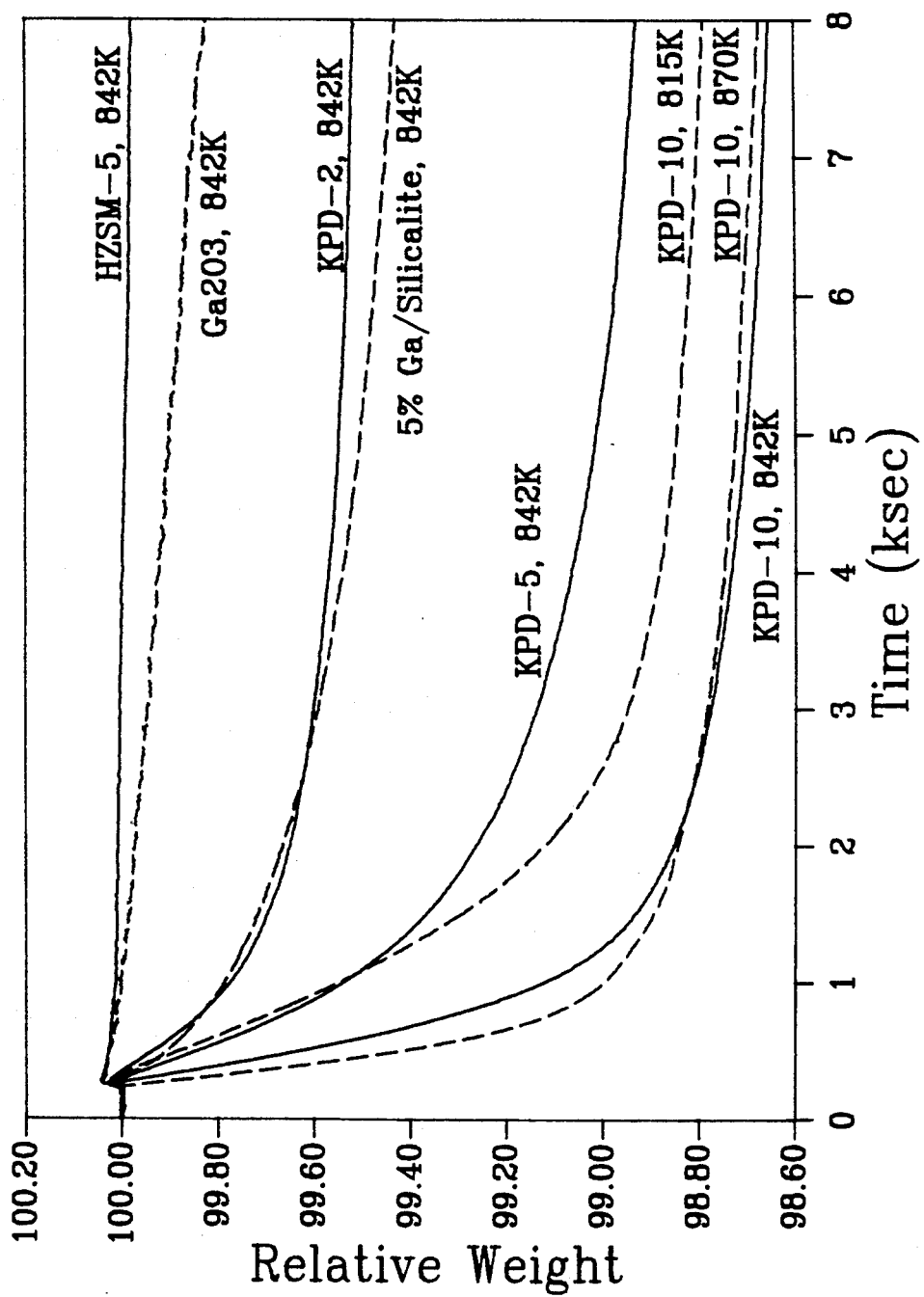
FIG. 4 illustrates the relative weight losses of several catalysts as a function of time during hydrogen reductions.

These results are shown in FIG. 4. Several important aspects should be noted. First, neither HZSM-5 nor $Ga_2O_3$ exhibited significant reduction individually. The effect of changing temperature for the KPD-10 series was as expected; a higher temperature yielded a higher initial rate of reduction, but the initial rate of reduction at 870 K. was only marginally larger than that at 842 K.

At a constant temperature of 842 K., the relative initial rates of reduction were highest for KPD-10, intermediate for KPD-5, and lowest for KPD-2. This order was the same order as the rate of catalyst activation by the propane reaction.

The relative weight loss for each of the KPD-10 samples was roughly the same. The KPD-5 sample showed a relative weight loss near, but slightly less than that of the KPD-10 samples. The relative weight loss for KPD-2 was clearly less than that for the KPD-10 and KPD-5 samples.

Comparing a 5% Ga/silicalite sample (Union Carbide S-115, 0.53% $Al_2O_3$) with the KPD-5 sample in FIG. 4 showed that the HZSM-5 base (with 3.73% $Al_2O_3$) promoted significantly more reduction than did the silicalite base (with only 0.53% $Al_2O_3$).

Figure 5:
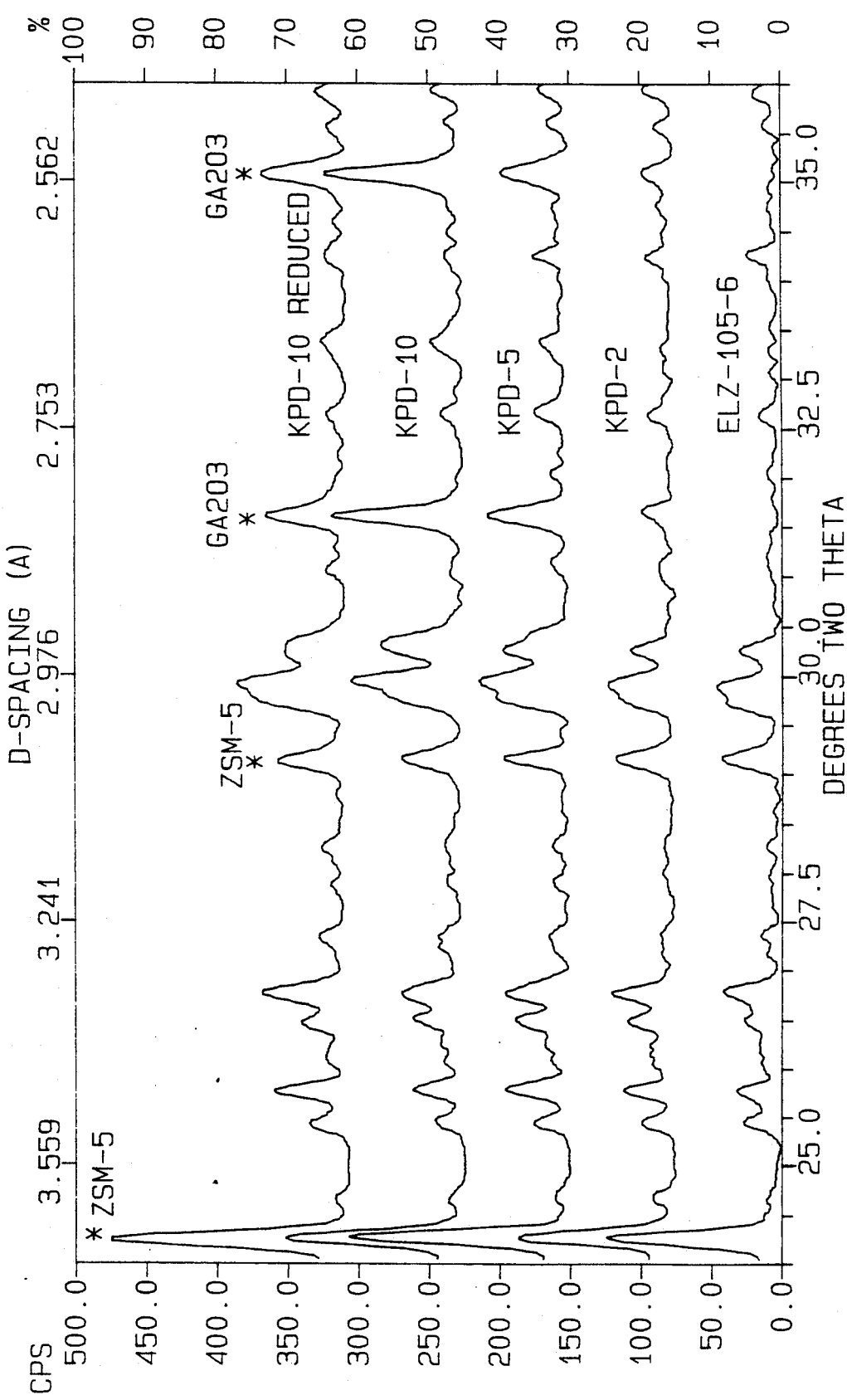
FIG. 5 illustrates portions of x-ray diffraction spectra of several catalysts.

The degree of reduction extracted from the microbalance data would provide all of the information needed to determine the reduction stoichiometry if the reduction processes were complete. However, complete reduction was not always the case, as may be seen from FIG. 5, which depicts the 24°–36° 2-theta region from the x-ray diffraction spectra. Two HZSM-5 bands at about 24.2° and 29.2° are highlighted in this figure, as are two $\beta$-$Ga_2O_3$ lines at about 31.6° and 35.1°. The HZSM-5 bands did not interfere with the $\beta$-$Ga_2O_3$ lines, and therefore these four bands were used as a measure of $Ga_2O_3$ content. Comparing the ELZ-105-6 (HZSM-5) spectrum with the KPD-2, KPD-5, and KPD-10 spectra (from catalyst samples which had been ball-milled, but not chemically treated), showed the relative $Ga_2O_3$ content growing as expected. Thus the ratio of the peak heights was used as a measure of $Ga_2O_3$ content; these results were expected to be at least semi-quantitative. The fifth spectrum in FIG. 5, denoted "KPD-10 REDUCED," represents a sample taken from an isothermal microbalance reduction experiment at $P_{H2}=23$ kPa, and 842 K. The relative intensities of the $Ga_2O_3$ lines were significantly reduced compared to the KPD-10 lines, but were clearly present. Table 8 summarizes the $Ga_2O_3$ content of a number of different samples taken from the microbalance.

TABLE 8

| Entry Numbers & Notes | Catalyst | % $Ga_2O_3$ | Cell Volume ($A^{°3}$) |
|---|---|---|---|
| Untreated Samples: | | | |
| 1 | HZSM-5 | — | 5372 |
| 2 | KPD-2 | 3.04 | 5372 |
| 3 | KPD-5 | 7.04 | 5364 |
| 4 | KPD-10 | 13.33 | 5368 |
| 5 | 5% Ga-Silicalite | 6.30 | 5345 |
| Microbalance Samples: | | | |
| 6 | HZSM-5 | 0 | 5362 |
| In He, 10K/min to 1000K | | | |
| 7 | HZSM-5 | 0 | 5345 |
| In He, 10K/min to 1250K | | | |
| 8 | HZSM-5 | 0 | 5363 |
| In $H_2$, 10K/min to 950K | | | |
| 9 | HZSM-5 | 0 | 5364 |
| In $H_2$, isothermal, 830K | | | |
| 10 | KPD-2 | 0.3 | 5377 |
| In $H_2$, 10K/min to 950K | | | |
| 11 | KPD-2 | 0.0 | 5370 |
| In $H_2$, 10K/min to 900K | | | |
| 12 | KPD-2 | — | — |
| In $H_2$, isothermal to 830K | | | |
| 13 | KPD-2 | 0.4 | 5377 |
| In $H_2$, isothermal to 830K | | | |
| 14 | KPD-5 | 0.0 | 5367 |
| In $H_2$, 10K/min, to 900K | | | |
| 15 | KPD-5 | 0.1 | 5371 |
| In $H_2$, 10K/min, to 900K | | | |
| 16 | KPD-5 | 2.4 | 5382 |
| In $H_2$, isothermal, 830K | | | |
| 17 | KPD-5 | 5.2 | 5366 |
| In $H_2$, isothermal, 830K | | | |
| 18 | KPD-10 | 7.0 | 5375 |
| In He, 10K/min to 900K | | | |
| 19 | KPD-10 | 7.5 | 5377 |
| In $H_2$, 10K/min to 900K | | | |
| 20 | KPD-10 | 8.9 | 5367 |
| In $H_2$, 10K/min to 900K | | | |
| 21 | KPD-10 | 10.2 | 5362 |
| In $H_2$, 10K/min to 900K | | | |
| 22 | KPD-10 | 6.9 | 5361 |
| In $H_2$, 10K/min to 900K | | | |
| 23 | KPD-10 | 9.0 | 5362 |
| In $H_2$, 3K/min to 900K | | | |
| 24 | KPD-10 | 7.6 | 5377 |
| In $H_2$, isothermal, 880K | | | |
| 25 | KPD-10 | 9.3 | 5366 |
| In $H_2$, isothermal, 780K | | | |
| 26 | KPD-10 | 0.6 | 5318 |
| In $H_2$, 10K/min to 1250K | | | |
| 27 | KPD-10 | 9.2 | 5374 |
| In $H_2$, isothermal 830K | | | |
| 28 | 5% Ga-Silicalite | 4.2 | 5345 |
| In $H_2$, isothermal, 830K | | | |

Notes:
Entries 2, 3, and 4 in Table 8 were used as standards for the calibration curve described above. The $Ga_2O_3$ and HZSM-5 were not ball-milled for the sample of entry 21.

The possibility was considered that chemical and thermal treatment of the KPD samples near reaction conditions promoted either substitution of Ga in the HZSM-5 lattice, or dealumination. Changes in unit cell size during the reduction of KPD catalysts could not be detected unless the treatment temperature was as high as 1250K. (See Table 8.) All unit cell sizes for the HZSM-5 catalysts fell in the range 5361 to 5382 $A^{°3}$, except for entries 7 and 26 in Table 8 (which had been heated to 1250° K., and showed a decline in cell size consistent with dealumination). To compare, note the silicalite samples, which showed a cell size of 5345 $A^{°3}$ (entries 5 and 28). This evidence suggests that the HZSM-5 crystalline matrix was not altered by $Ga_2O_3$ loading and reduction.

The above evidence suggests an interaction between $Ga_2O_3$ and HZSM-5 in the presence of hydrogen, even when the hydrogen is itself supplied by the propane aromatization reaction. Furthermore, this interaction leads to the formation of a modified zeolite system which possesses novel catalytic properties. Known gallium chemistry suggests that $Ga_2O_3$ can undergo reduction by $H_2$ at 873K to form the suboxide, $Ga_2O$, which is a dark-brown to black amorphous substance, stable in dry air. See e.g., Sheka, I.A., et al., The Chemistry of Gallium (1966), which is incorporated by reference. This reduction process apparently occurred directly in the TPR-microbalance studies, but at substantially lower temperatures. The reduction evidently involved acidic zeolite lattice sites, because (1) no reduction took place with pure $Ga_2O_3$ or with $Ga_2O_3$ on a NaX zeolite substrate, and (2) $Ga_2O_3$/silicalite showed only a very limited reduction of $Ga_2O_3$. These studies showed that the intimacy of the $Ga_2O_3$/HZSM-5 mixing, hydrogen partial pressure, temperature, temperature programming rate, and zeolite acidity are all factors which can influence the reduction processes.

The degree of reduction of $Ga_2O_3$, and the weight loss as determined by microbalance, can be coupled as follows:

$$\frac{(W_i - W_e)}{MW(Ga_2O_3)} = \frac{\beta}{MW_x}$$

$MW(Ga_2O_3) = 188$ gr/mole.

-continued $MW_x$ = molecular weight of the volatile component of the reduction products.
$\beta$ = percentage weight loss from the microbalance.
$W_i$ = initial $Ga_2O_3$ loading in weight %.
$W_e$ = $Ga_2O_3$ content at the end of the reduction $(W_i-W_e)$ was determined from the x-ray data, and $\beta$ from the microbalance data. The unknown in this equation, $MW_x$, could then be extracted from a plot of $\beta$ versus $(W_i-W_e)$, as illustrated in FIG. 6.

Figure 6:
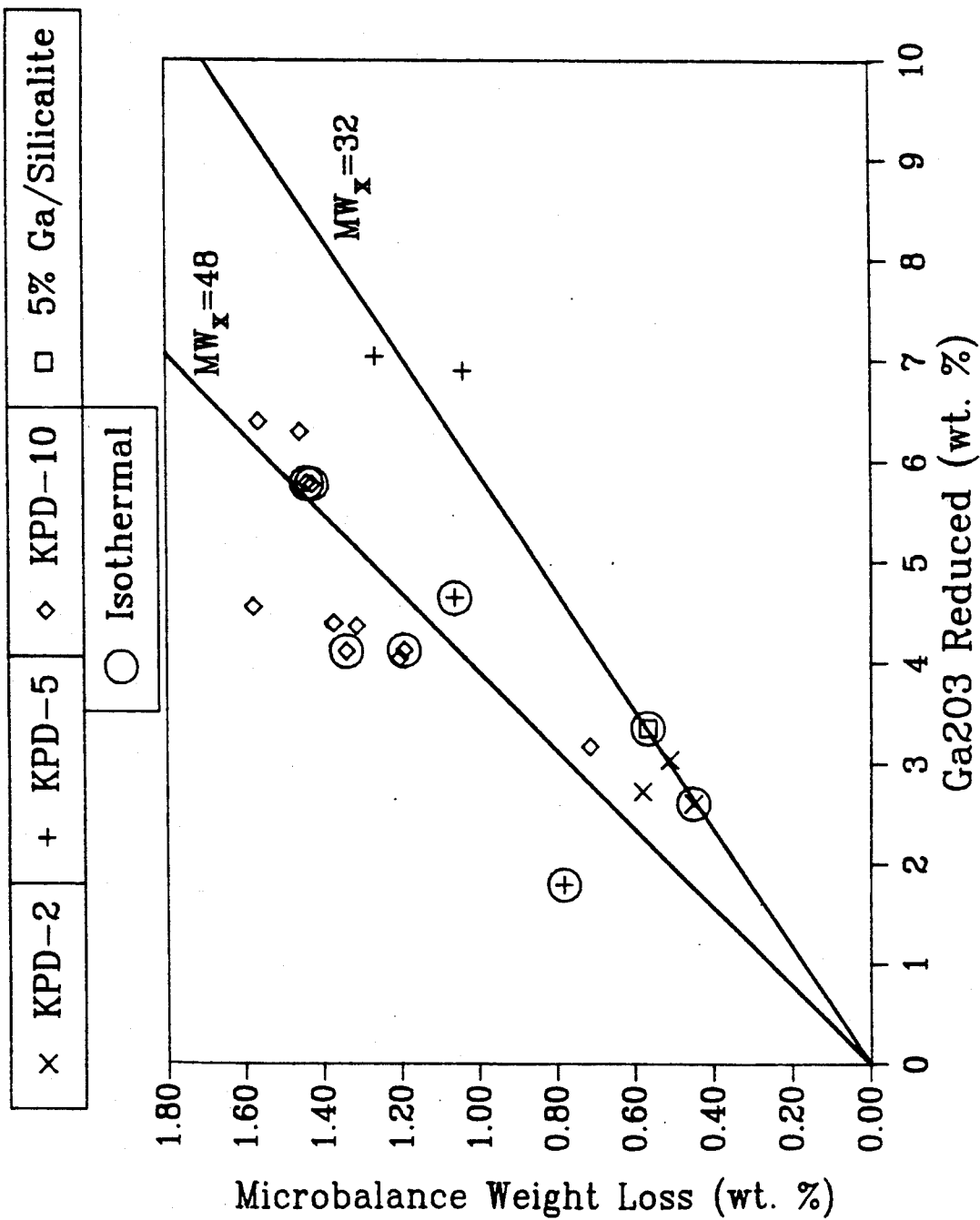
FIG. 6 illustrates a plot of microbalance weight loss percentages during hydrogen reduction, versus weight percentage of $Ga_2O_3$ reduced.

The data in FIG. 6 are scattered, primarily as a result of the semi-quantitative nature of the determination of $(W_i-W_e)$ by x-ray diffraction. Also contributing to the scatter is the overlapping of the weight loss due to water of hydration and dehydroxylation of HZSM-5 from the weight loss due to reduction. The isothermal weight loss experiments should provide the most accurate data for the determination of $\beta$; these points are circled in FIG. 6. Even for the KPD-10 samples, which contained in excess of 13 weight % $Ga_2O_3$ (10 weight % Ga on an elemental basis), only about 6.5 weight % of $Ga_2O_3$ appeared to be reduced. This observation suggested that the HZSM-5 was a stoichiometric reactant in the reduction process. Lines representing $MW_x=32$ and $MW_x=48$ are shown in FIG. 6. $MW_x$ was clearly greater than 32, and $MW_x=48$ fit the scattered data rather well. This figure suggests that three water molecules constitute the volatile product of the reduction process (noting that the hydgrogen in the water molecule is supplied by the gas phase reactant, and therefore will not appear as a weight loss from the solid).

With these observations in hand, the inventors hypothesize the following reduction process:

(1) $Ga_2O_3 + 2H_2 \longrightarrow Ga_2O + 2H_2O$, and

(2a) $Ga_2O + H_2 \longrightarrow 2Ga + H_2O$ or

(2b) $Ga_2O + 2H^+Z^- \longrightarrow 2Ga^+Z^- + H_2O$ where $H^+Z^-$ is a proton associated with the anionic zeolite ($Z^-$). Step (1) follows from known Ga chemistry, in that $Ga_2O$ is a product of the reduction of $Ga_2O_3$ with hydrogen. Step (2a) is possible, to the extent that the x-ray diffraction/microbalance correlation is correct, but there is no reason to expect that this process should end with a 6.5 weight % $Ga_2O_3$ limit for KPD-10 samples.

We prefer path (2b), which imposes an upper limit on $Ga_2O_3$ reduction due to the zeolite framework. Because this proposed process requires two protons from the HZSM-5 solid, one would expect $MW_x=50$ rather than 48, but the inventors were unable to statistically distinguish 50 from 48 with the experimental scatter in FIG. 6. Furthermore, using the stoichiometric analysis with 3.73 weight % $Al_2O_3$ for the HZSM-5, and assuming one proton per Al atom, an upper an upper reduction limit of 6.04% $Ga_2O_3$ (i.e., the $Ga_2O_3$ content may be reduced from 13.33% to 7.29%) was computed for the KPD-10 catalyst, which agreed quite well with the observed maximum of 6.5% when possible inaccuracies were taken into account. KPD-5 samples can theoretically undergo 6.47% $Ga_2O_3$ reduction based upon an $Al_2O_3$ stoichiometric limit, and up to 7% reduction has been observed.

The 5% Ga/Silicalite samples presented a problem under this model. A microbalance weight decline of 0.24 weight % was expected if 0.53% $Al_2O_3$ limited the reduction, but the silicalite was observed to promote a 0.59 weight % decline. The inventors hypothesize that silanol groups within the silicalite were responsible for promoting the $Ga_2O_3$ reduction beyond the known $Al_2O_3$ content, and that the silanol groups provided protons for Step (2b). The fact that the silicalite base promoted less $Ga_2O_3$ reduction than a similarly loaded HZSM-5 base is evidence that the zeolite was a stoichiometric reactant in the reduction process.

Another possibility is that Ga replaced Al in the zeolite lattice during reduction. However, replacement of Ga for Al should yield a unit cell expansion, which has not been observed. Nevertheless, the inventors have considered the possibility that there was a compensation effect, in which $Al_2O_3$ was removed in excess (resulting in a lattice contraction), and in which Ga replaced only a portion of the $Al_2O_3$ (resulting in a compensating lattice expansion). This situation is very unlikely, in view of the evidence for a 1:1 Ga:Al interaction.

The microbalance and x-ray diffraction experiments showed that the reduction process occurred even at hydrogen partial pressures as low as 2.5 kPa. Under propane reactant flow, the partial pressure of molecular hydrogen due to reaction should not have exceeded an estimated 0.1 kPa. There is a question whether such low $H_2$ pressures could promote the reduction process via molecular hydrogen on time scales similar to the observed transient time scale for aromatization enhancement, or whether another reduction mechanism operated with a different type of active hydrogen. The inventors have found no reason so far as to exclude either possibility.

An interesting feature of the kinetic results was that the time scale for the propane-initiated activation (without $H_2$ pretreatment) was shorter for higher $Ga_2O_3$ loadings. (See Table 5.) This observation suggests that the activation process was not limited by active or molecular hydrogen, but by the transport of Ga species into the zeolite. This transport was probably a solid state process, rather than one involving the volatilization of a Ga species, because an intimate mixture of $Ga_2O_3$ with HZSM-5 was required before reduction was observed.

A "cation site" of a zeolite is a site of an exchangable or exchanged cation, as described in U.S. Pat. No. 3,702,886, which is incorporated by reference. The location of such a cation site may not necessarily be a geometrically fixed location on the zeolite structure. Cations at such a site may include $NH_4^+$ or $H^+$ before reaction, and are believed to include $Ga^+$ (gallium(I)) after reaction according to the preparation method of the present invention.

Without wishing to be bound by this theory, the inventors have therefore concluded that a distinguishing feature of a catalyst of the present invention is the formation of a zeolite comprising $Ga^+$ on the zeolite's cation sites. Other preparation techniques, such as ion-exchange or impregnation with gallium salts, will disturb the cationic makeup within the zeolite pore prior to gallium substitution because of the aqueous treatment, resulting in the incorporation or association of $Ga^{+3}$ rather than $Ga^+$. The inventors hypothesize that the preparation method of the present invention incorporates the maximum useful amount of $Ga^+$ into the zeolite's cation sites, or close to that maximum amount.

We claim:

1. A catalyst prepared by the step of making an intimate mechanical mixture of:
   (a) a zeolite with a pore mouth comprising 10 oxygen atoms; and
   (b) a compound comprising gallium;
   wherein gallium has been transported into the zeolite structure at a cation site.

2. A catalyst as recited in claim 1, wherein said zeolite is selected from the group consisting of ZSM-5, ZSM-11, and ZSM-12.

3. A catalyst as recited in claim 1, wherein said zeolite comprises ZSM-5.

4. A catalyst as recited in claim 1, wherein said compound is selected from the group consisting a gallium salts, alkali metal gallates, gallium oxide, and gallium suboxide.

5. A catalyst as recited in claim 1, wherein said compound comprises gallium oxide.

6. A catalyst as recited in claim 1, wherein the process for preparing said catalyst additionally comprises the step of reducing said intimate mechanical mixture.

7. A catalyst as recited in claim 6, wherein said reducing comprises reacting said intimate mechanical mixture with hydrogen gas.

8. A catalyst as recited in claim 1, wherein said zeolite comprises ZSM-5, and wherein said compound comprises gallium oxide.

9. A catalyst as recited in claim 8, wherein the process for preparing said catalyst additionally comprises the step of reducing said intimate mechanical mixture.

10. A catalyst as recited in claim 9, wherein said reducing comprises reacting said intimate mechanical mixture with hydrogen gas.

11. A catalyst prepared by making an intimate mechanical mixture of:
    (a) a zeolite with a pore mouth comprising 10 oxygen atom; and
    (b) a compound comprising gallium;
    wherein said zeolite has at least one cation site comprising gallium (I).

12. A catalyst as recited in claim 11, wherein said zeolite is selected from the group consisting of ZSM-5, ZSM-11, and ZSM-12.

13. A catalyst as recited in claim 11, wherein said zeolite comprises ZSM-5.

14. A catalyst as recited in claim 11, wherein said zeolite has a plurality of cation sites consisting essentially of gallium(I).

15. A catalyst as recited in claim 14, wherein said zeolite is selected from the group consisting of ZSM-5, ZSM-11, and ZSM-12.

16. A catalyst as recited in claim 14, wherein said zeolite comprises ZSM-5.

17. A catalyst as recited in claim 11, wherein at least 75% of the gallium is present as gallium(I) on a cation site of said zeolite.

18. A catalyst as recited in claim 17, wherein said zeolite is selected from the group consisting of ZSM-5, ZSM-11, and ZSM-12.

19. A catalyst as recited in claim 17, wherein said zeolite comprises ZSM-5.

* * * * *